(12) United States Patent
Vorlop et al.

(10) Patent No.: US 10,005,748 B2
(45) Date of Patent: Jun. 26, 2018

(54) 5-HYDROXYMETHYLFURFURAL PRODUCTION USING A MULTI-FLUORINATED ALCOHOL COMPOUND

(71) Applicants: Klaus-Dieter Vorlop, Braunschweig (DE); Ulf Prüsse, Braunschweig (DE)

(72) Inventors: Klaus-Dieter Vorlop, Braunschweig (DE); Ulf Prüsse, Braunschweig (DE); Ramona Krieg, Warberg (DE); Linda Teevs, Braunschweig (DE)

(73) Assignees: Klaus-Dieter Vorlop, Braunschweig (DE); Ulf Pruesse, Braunschweig (DE)

( * ) Notice: Subject to any disclaimer, the term of this patent is extended or adjusted under 35 U.S.C. 154(b) by 0 days. days.

(21) Appl. No.: 15/517,548

(22) PCT Filed: Oct. 9, 2015

(86) PCT No.: PCT/EP2015/073367
§ 371 (c)(1),
(2) Date: Apr. 7, 2017

(87) PCT Pub. No.: WO2016/055608
PCT Pub. Date: Apr. 14, 2016

(65) Prior Publication Data
US 2017/0305872 A1    Oct. 26, 2017

(30) Foreign Application Priority Data
Oct. 9, 2014   (DE) .................. 10 2014 220 517

(51) Int. Cl.
| | | |
|---|---|---|
| *C07D 307/46* | (2006.01) | |
| *B01J 27/053* | (2006.01) | |
| *B01J 31/10* | (2006.01) | |
| *C07D 307/36* | (2006.01) | |
| *C07D 307/68* | (2006.01) | |
| *B01J 27/10* | (2006.01) | |
| *B01J 23/52* | (2006.01) | |

(52) U.S. Cl.
CPC ............ *C07D 307/46* (2013.01); *B01J 23/52* (2013.01); *B01J 27/053* (2013.01); *B01J 27/10* (2013.01); *B01J 31/10* (2013.01); *C07D 307/36* (2013.01); *C07D 307/68* (2013.01)

(58) Field of Classification Search
CPC .................................................... C07D 307/46
USPC ......................................................... 549/485
See application file for complete search history.

(56) References Cited

FOREIGN PATENT DOCUMENTS

| CN | 102430265 A | 5/2012 |
|---|---|---|
| WO | 2007/146636 A1 | 6/2007 |

OTHER PUBLICATIONS

Roman-Leshkov et al., "Production of dimethylfuran for liquid fuels from biomass-derived carbohydrates", Nature, 2007, pp. 982-986, vol. 447.
Roman-Leshkov et al., "Phase Modifiers Promote Efficient Production of Hydroxymethylfurfural from Fructose", Science, 2006, pp. 1933-1937, vol. 312, No. 5782.
Hansen et al., "Synergy of boric acid and added salts in the catalytic dehydration of hexoses to 5-hydroxymethylfurfural in water", Green Chemistry, 2011, pp. 109-115, vol. 13.
Roman-Leshkov et al., "Solvent Effects on Fructose Dehydration to 5-Hydroxymethylfurfural in Biphasic Systems Saturated with Inorganic Salts", Topics in Catalysis, 2009, pp. 297-303, vol. 52.

*Primary Examiner* — Taofiq A Solola
(74) *Attorney, Agent, or Firm* — Whitham, Curtis & Cook, P.C.

(57) ABSTRACT

The present invention relates to a process for producing a water cleavage product, a water cleavage product thus produced, a process for producing at least one water cleavage secondary product, a water cleavage secondary product thus produced and the use of a multi-fluorinated alcohol compound for the extraction of at least one water cleavage product from an aqueous phase.

22 Claims, No Drawings

5-HYDROXYMETHYLFURFURAL PRODUCTION USING A MULTI-FLUORINATED ALCOHOL COMPOUND

The present invention relates to a process for producing a water cleavage product, to a water cleavage product thus produced, to a process for producing at least one water cleavage conversion product, to a water cleavage conversion product thus produced and to the use of a multi-fluorinated alcohol compound for extracting at least one water cleavage product from an aqueous phase.

5-hydroxymethylfurfural is an important intermediate on the route from renewable raw materials to otherwise petrochemically based polymer building blocks. For the conversion of carbohydrates to 5-hydroxymethylfurfural, also referred to as HMF, some technologies are available in the prior art. However, an economical manufacturing process for HMF and its conversion products, such as furandicarboxylic acid, also known as FDCA, with which a chemical industry based on renewable raw materials can be built, is lacking so far. The development of a cost-effective and effective manufacturing method for HMF has been a problem for science for more than 100 years. For the production of HMF, for example, water is used for ecological and cost reasons and because of the good solubility of sugars (starting materials in HMF production).

The synthesis of HMF, especially by acid-catalyzed, three-fold dehydration, also referred to as water cleavage, of hexoses, mainly fructose, is very complex so that numerous secondary and degradation reactions such as isomerization, fragmentation and condensation can occur, which limits the yield of HMF. By using organic solvents, such as DMSO, DMF and sulfolane, or ionic liquids, the formation of degradation products is in fact reduced or even prevented and an increased HMF yield is obtained. However, the separation or isolation of the HMF obtained from these reaction mixtures creates major problems. In addition, ionic liquids have a very limited regenerability, which leads to unacceptable costs.

By means of the alternative or additional use of extractants or extractant mixtures, HMF can be removed from the aqueous reaction phase and thus limiting of the yield due to degradation and by-product formation can be minimized. Extractants, such as methyl isobutyl ketone, or extraction mixtures, such as a mixture of methyl isobutyl ketone and 2-butanol, used in the prior art have low extraction capacity and high boiling points so that product isolation is more difficult and thus are not an efficient system for HMF production.

CN 102430265 A discloses an aqueous two-phase extraction system containing an anionic surfactant, a cationic surfactant, hexafluoroisopropanol and water.

Andrea Di Salvo et al. (Adv. Synth. Catal., 2006, 348, 118-124) disclose a nucleophilic addition of hexafluoro-2-propanol to vinyl ethers.

In addition to HMF, other intermediates or end products which are of interest to the chemical industry can be produced from carbohydrates or derivatives thereof. In all these reactions, it is critical that the reaction terminates at the desired intermediate or end product and that no subsequent reaction occurs under the present reaction conditions, in particular under the acidic conditions, and the desired product is obtained on the one hand in high yield but also with high selectivity.

An appropriate reaction system has not hitherto been known from the prior art. None of the processes known from the prior art makes it possible to selectively cleave single or multiple water molecules from carbohydrates or derivatives thereof under acid catalysis, so as to obtain in high yields and selectively a product produced by the sole cleavage of water and, if appropriate, further reactions occurring in acid-catalyzed cleavage of water.

It is therefore the object of the present invention to overcome in particular the above-mentioned disadvantages, in particular to provide a process by which a product of a water cleavage compound having at least one hydroxyl group cleavable in an acid-catalyzed manner, preferably of carbohydrates or derivatives thereof, can be prepared in high yield and/or selectivity.

The object of the present invention is achieved in particular by the technical teaching of the independent claims.

The object is achieved in particular by a process for producing at least one water cleavage product, comprising the following steps:
a) providing at least one water cleavage compound having at least one hydroxyl group cleavable in an acid-catalyzed manner,
b) acid-catalyzed cleavage of water from the at least one water cleavage compound provided in step a) in a reaction system having at least one phase, wherein one phase comprises at least one multi-fluorinated alcohol compound having the structural formula I below:

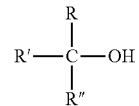

where
(i) R, R' and R" are mutually independently selected from the group consisting of H, aryl, alkyl, alkenyl, alkynyl, F, —$CF_2X$, —$C_nF_{2n}X$, —$C_nF_{2n-2}X$, wherein at least one, preferably at least two, of the radicals R, R' and R" is/are other than H, aryl, alkyl, alkenyl and alkynyl, n is an integer and has values from 2 to 6 and X=H, F or Cl, or
(ii) R and R' are covalently bonded to each other and form a chain having an empirical formula which is selected from the group consisting of —$C_mF_{2m-1}X$, —$C_mF_{2m-2}X$, —$C_mF_{2m-3}X$, —$C_mF_{2m-4}X$ and —$C_mF_{m-1}X$ and where R" is selected from the group consisting of H, aryl, alkyl, alkenyl, alkynyl, F, —$CF_2X$, —$C_nF_{2n-2}X$ and —$C_nF_{2n-2}X$, where n is an integer and has values from 2 to 6, where X=H, F or Cl and where m is an integer and has values from 3 to 7, or where R" is not present if a double bond is present on the carbon atom adjacent to the OH; and
c) obtaining at least one water cleavage product produced by the acid-catalyzed cleavage of water according to step b).

In the context of the present invention, "carbohydrates" are understood to mean polyhydroxyaldehydes and polyhydroxyketones and also higher molecular weight compounds which can be converted into such compounds by hydrolysis. The term "carbohydrate" also includes derivatives, i.e. derivatives of a carbohydrate, which are formed from the carbohydrate in one or more reaction steps. Preference is given to "carbohydrates" as meaning polyhydroxyaldehydes and polyhydroxyketones and also higher molecular weight compounds which can be converted into such compounds by hydrolysis.

In the context of the present invention, the term "oligosaccharides" is understood to mean a carbohydrate having, preferably consisting of, 3 to 20, preferably 3 to 10, monosaccharide units, which are linked to one another in each case by a glycosidic bond. In the context of the present invention, "oligosaccharides" are also understood to mean derivatives, i.e. derivatives of an oligosaccharide which are formed from one oligosaccharide in one or more reaction steps. The term "oligosaccharide" is preferably understood to mean a carbohydrate having, preferably consisting of, 3 to 20, preferably 3 to 10, monosaccharide units.

According to the invention, the term "polysaccharide" is understood to mean carbohydrates having, preferably consisting of, at least 11, preferably at least 21 monosaccharides which are linked to one another in each case via a glycosidic bond. In the context of the present invention, "polysaccharides" are also understood to mean derivatives, i.e. derivatives of a polysaccharide which are formed from one polysaccharide in one or more reaction steps. According to the invention, the term "polysaccharides" is preferably to be understood as meaning carbohydrates having, preferably consisting of, at least 11, preferably at least 21, monosaccharides, which are linked to one another in each case via a glycosidic bond.

The term "carbohydrate derivative" is understood to mean a derivative of a carbohydrate which can be formed from a carbohydrate in one or more reaction steps. For the production of a carbohydrate derivative, a carbohydrate is preferably oxidized and/or reduced alone. It is alternatively preferable for the carbohydrate derivative to be able to be prepared from a carbohydrate by a fermentative and/or a catalytic process. Preferably, the carbohydrate derivative has a hydroxyl or carboxyl group instead of the aldehyde group compared to the corresponding carbohydrate. Alternatively or additionally, the carbohydrate derivative preferably has, compared to the corresponding carbohydrate, at at least one position, preferably at exactly one position, a hydrogen atom or an $NHR^1$ group instead of a hydroxyl group, where $R^1$ is hydrogen, alkyl, alkenyl or alkynyl, preferably H, C1 to C8-alkyl, C1 to C8-alkenyl or C1 to C8-alkynyl. Alternatively or additionally the carbohydrate derivative preferably has a carboxyl group instead of the terminal $CH_2OH$ group compared to the corresponding carbohydrate. Alternatively or additionally, the carbohydrate derivative preferably has one or more, preferably precisely one hydroxyl group which is sulfonated, esterified or etherified, compared to the corresponding carbohydrate.

In the context of the present invention, a "water cleavage compound having at least one hydroxyl group cleavable in an acid-catalyzed manner" is understood to mean a compound in which at least one, preferably one to three, hydroxyl groups can be cleaved off under the reaction conditions according to the invention or preferred according to the invention. Preferably, the at least one hydroxyl group can be cleaved from the water cleavage compound at a pH of less than 7, preferably less than 5, preferably less than 3, preferably less than 1. It is alternatively or additionally preferable for the at least one hydroxyl group to be able to be cleaved off at a temperature of at most 200° C., preferably at most 100° C. It is alternatively or additionally preferable for the at least one hydroxyl group to be able to be cleaved off at a pressure of from 0.001 mbar to 5 bar. According to the invention, a "hydroxyl group cleavable in an acid-catalyzed manner" is preferably understood to mean a hydroxyl group which can be cleaved off in a reaction mixture of water and hexafluoroisopropanol in a volume ratio of 1:3 at a pH of less than 1 at a temperature of 65° C. and a pressure of 1013 mbar in less than 8 hours, preferably less than 3 hours.

The term "immobilized on a support material" in the context of the present invention is understood to mean that the multi-fluorinated alcohol compound according to the invention or preferred according to the invention is fixed to a support material. Immobilization is preferably carried out by adsorption or by covalent bonding to a carrier material. The immobilization is preferably carried out by covalent bonding to a support material. The support material used is preferably a polyalkylhydrosiloxane, an alkylated metal oxide, a metal oxide or a mixture thereof. The metal oxide is preferably $SiO_2$, $TiO_2$ or $Al_2O_3$. In the case of adsorption, fixing is effected solely by intermolecular interactions, preferably by Van-der-Waals forces. If a covalent bond is present between the multi-fluorinated alcohol compound according to the invention or preferred according to the invention and the carrier material, this bonding is preferably effected by addition of elements present in the support material, preferably O, N, S or Si, to a double bond or triple bond present in the multi-fluorinated alcohol compound. The multi-fluorinated alcohol compound immobilized on a support material preferably has a covalent bond to the support material instead of exactly one element present in the radicals R, R' and R" in the structural formula I which is selected from hydrogen, fluorine and chlorine.

It is preferably provided that the aryl, alkyl, alkenyl or alkynyl present in the multi-fluorinated alcohol compound is an aryl, alkyl, alkenyl or alkynyl immobilized on a support material. In this case, the aryl, alkyl, alkenyl or alkynyl group is preferably bonded to the support material via at least one, preferably exactly one, covalent bond.

In the context of the present invention, the term "water cleavage product" is understood to mean a compound which is obtained from a water cleavage compound solely by single or multiple cleavage of water and, if appropriate, by further reactions occurring during the acid-catalytic cleavage of water according to step b).

According to the invention, a process is provided wherein, in a reaction system under acid catalysis, preferably under acidic conditions, i.e. at a pH of less than 7, said system having at least one phase, preferably at least two phases, preferably exactly two phases, single or multiple water molecules are cleaved off from the water cleavage compound having a hydroxyl group cleavable in a acid-catalyzed manner. The reaction system has one phase comprising at least one multi-fluorinated alcohol compound according to structural formula I and optionally immobilized on a support, preferably at least to 50% by volume. The phase comprising at least one multi-fluorinated alcohol compound can function on the one hand as a reaction phase, that is to say as a phase in which the acid-catalyzed cleavage of water from the at least one water cleavage compound takes place according to step b). However, this phase can also serve as an extraction phase if a further phase, preferably an aqueous phase, is present in which the acid-catalyzed cleavage of water from the water cleavage compound is preferably carried out.

Surprisingly, it has been found here that the presence of at least one multi-fluorinated alcohol compound in a reaction system for acid-catalyzed cleavage of water from a water cleavage compound advantageously results in a water cleavage product in high yield and conversion rate and also with high selectivity.

Surprisingly, it has also been found that by the addition of at least one acid and/or at least one salt, a phase separation can be induced between the aqueous phase and the phase comprising at least one multi-fluorinated alcohol compound, if this phase separation is not already present. In particular, a phase separation between an aqueous phase and a phase containing hexafluoroisopropanol can thereby be induced. Surprisingly, by means of the phase induction, it is possible to allow the acid-catalytic cleavage of water from the water cleavage compound according to step b) to proceed in the aqueous phase and to extract the water cleavage product effectively using the phase comprising at least one multi-fluorinated alcohol compound.

It has also surprisingly been found that the phase containing at least one multi-fluorinated alcohol compound extracts in an effective and highly selective manner the water cleavage product from an aqueous phase in which the acid-catalytic cleavage of water from a water cleavage compound takes place, and in addition prevents the further reaction, preferably a condensation or hydrolytic cleavage, of the water cleavage product. Preferably, extraction of the HMF from the aqueous phase prevents its hydrolytic cleavage to formic acid and levulinic acid and/or its condensation to form humins.

In particular, the multi-fluorinated alcohol compounds according to the invention have a significantly higher distribution coefficient $K_x$ ($K_x = c(X)$ in the multi-fluorinated alcohol compound phase/$c(X)$ in the aqueous phase) for the water cleavage product X, preferably greater than 5, preferably greater than 20, compared to extractants known from the literature such as methyl isobutyl ketone. For example, the distribution coefficient $K_{HMF}$ for HMF with the multi-fluorinated alcohol compounds is at least 5 compared to methyl isobutyl ketone where $K_{HMF}$ is about 1 (see Y. Roman-Leshkov et al., Science, 2006, 312, 1933 and T. S. Hansen et al., Green Chem., 2011, 13, 109 to 114). By virtue of the higher distribution coefficient, the same amount of water cleavage product can be extracted from the aqueous phase with a smaller amount of multi-fluorinated alcohol compounds compared to extractants known from the literature. Thus, extractant can be saved.

The water cleavage product is therefore extracted from the aqueous phase with high selectivity according to the invention by the phase which comprises preferably predominantly, preferably at least to 50% by volume, preferably at least to 70% by volume, the at least one multi-fluorinated alcohol compound. The water cleavage compound, preferably the carbohydrate or the carbohydrate derivative, is preferably extracted by the multi-fluorinated alcohol compound in very small amounts or not at all from the aqueous phase and remains in the aqueous phase, preferably at least to 95%, preferably at least to 99%, preferably to 100%.

It is preferably provided that the multi-fluorinated alcohol compound has the structural formula I below:

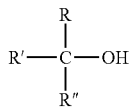

where
(i) R, R' and R" are mutually independently selected from the group consisting of H, C3-C10 aryl, preferably C6-C8 aryl, C1-C30 alkyl, preferably C1-C8 alkyl, C1-C30 alkenyl, preferably C1-C8 alkenyl, C1-C30 alkynyl, preferably C1-C8 alkynyl, F, —CF$_2$X, —C$_n$F$_{2n}$X, —C$_n$F$_{2n-2}$X, wherein at least one, preferably at least two of the radicals R, R' and R" is/are other than H, C3-C10 aryl, preferably C6-C8 aryl, C1-C30 alkyl, preferably C1-C8 alkyl, C1-C30 alkenyl, preferably C1-C8 alkenyl and C1-C30 alkynyl, preferably C1-C8 alkynyl, n is an integer and has values from 2 to 6 and X=H, F or Cl, or (ii) R and R' are covalently bonded to each other and form a chain having an empirical formula which is selected from the group consisting of —C$_m$F$_{2m-1}$X, —C$_m$F$_{2m-2}$X, —C$_m$F$_{2m-3}$X, —C$_m$F$_{2m-4}$X and —C$_m$F$_{m-1}$X and where R" is selected from the group consisting of H, C3-C10 aryl, preferably C6-C8 aryl, C1-C30 alkyl, preferably C1-C8 alkyl, C1-C30 alkenyl, preferably C1-C8 alkenyl, C1-C30 alkynyl, preferably C1-C8 alkynyl, F, —CF$_2$X, —C$_n$F$_{2n}$X and —C$_n$F$_{2n-2}$X, where n is an integer and has values from 2 to 6, where X=H, F or Cl and where m is an integer and has values from 3 to 7, or where R" is not present if a double bond is present on the carbon atom adjacent to the OH.

In accordance with (i), R' is preferably selected from F, —CF$_2$X, —C$_n$F$_{2n}$X and —C$_n$F$_{2n-2}$X, where n is an integer and has values from 2 to 6 and X=H, F or Cl.

In accordance with (i), R and R' are preferably selected from F, —CF$_2$X, —C$_n$F$_{2n}$X and —C$_n$F$_{2n-2}$X, where n is an integer and has values from 2 to 6 and X=H, F or Cl.

In accordance with (i), R, R' and R" are preferably selected from F, —CF$_2$X, —C$_n$F$_{2n}$X and —C$_n$F$_{2n-2}$X, where n is an integer and has values from 2 to 6 and X=H, F or Cl.

The multi-fluorinated alcohol compound is preferably an unsupported, non-immobilized multi-fluorinated alcohol compound.

Preferably at least one, preferably at least two, of the radicals R, R' and R" according to (i)" is/are other than H, F, aryl, alkyl, alkenyl and alkynyl.

The aryl, alkyl, alkenyl and alkynyl radicals are preferably unsubstituted and consist solely of carbon and hydrogen atoms.

Preference is given to providing a process in which the water cleavage compound having at least one hydroxyl group cleavable in an acid-catalyzed manner is a carbohydrate, a carbohydrate derivative or a mixture thereof.

The water cleavage product is preferably a carbohydrate product, a carbohydrate product derivative or a mixture thereof.

The at least one carbohydrate is preferably selected from monosaccharides, disaccharides, oligosaccharides and polysaccharides.

The monosaccharide is preferably in the D- or L-form, preferably in the D-form.

The carbohydrate derivative is preferably selected from lactic acid (2-hydroxypropionic acid), 2,3-butanediol, 1,4-butanediol, hydroxypropionaldehyde and 3-hydroxypropionic acid.

The carbohydrate derivative is preferably additionally or alternatively a polysaccharide derivative, preferably selected from chitin, starch, preferably α-amylose, glycogen, glycosaminoglycans, preferably chondroitin sulfate, dermatan sulfate, keratin sulfate, heparin and hyaluronic acid.

Preference is given to using fructose-containing carbohydrates or carbohydrate derivatives in step a). The carbohydrate is preferably fructose, difructose, trifructose, inulin, sucrose, isomaltulose, oligofructose or a mixture thereof.

The carbohydrate provided in step a) is preferably a carbohydrate comprising, preferably consisting of, monomer units which can isomerize to fructose. Preferably, such carbohydrates are carbohydrates which contain glucose or carbohydrates consisting of glucose. Preferred glucose-containing carbohydrates are glucose, sucrose, isomaltulose, cellobiose, cellulose, starch, hydrolyzed starch, amylopectin or a mixture thereof.

The carbohydrates, carbohydrate derivatives or mixtures thereof are preferably in the form of a syrup.

Preferably, a process is provided wherein the at least one carbohydrate is a compound containing hexose and/or pentose.

Preferably, a process is provided wherein the hexose and/or pentose is selected from the group consisting of fructose, glucose, arabinose and xylose.

Preferably, a process is provided for producing 5-hydroxymethylfurfural comprising the following steps:
  a) providing at least one glucose-containing and/or fructose-containing carbohydrate or a derivative thereof, preferably fructose,
  b) acid-catalyzed, three-fold cleavage of water from the at least one glucose-containing and/or fructose-containing carbohydrate or derivative thereof provided in step a), preferably from fructose, preferably after isomerization of glucose to fructose and/or cleavage of at least one glycosidic bond, in a biphasic reaction system, wherein one phase comprises water and the other phase comprises at least one multi-fluorinated alcohol compound having the structural formula I below:

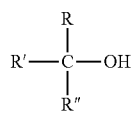

where
  (i) R, R' and R" are mutually independently selected from the group consisting of H, aryl, alkyl, alkenyl, alkynyl, F, —$CF_2X$, —$C_nF_{2n}X$, —$C_nF_{2n-2}X$, wherein at least two of the radicals R, R' and R" are other than H, aryl, alkyl, alkenyl and alkynyl, n is an integer and has values from 2 to 6 and X=H, F or Cl, or
  (ii) R and R' are covalently bonded to each other and form a chain having an empirical formula which is selected from the group consisting of —$C_mF_{2m-1}X$, —$C_mF_{2m-2}X$, —$C_mF_{2m-3}X$, —$C_mF_{2m-4}X$ and —$C_mF_{m-1}X$ and where R" is selected from the group consisting of H, aryl, alkyl, alkenyl, alkynyl, F, —$CF_2X$, —$C_nF_{2n}X$ and —$C_nF_{2n-2}X$, where n is an integer and has values from 2 to 6, where X=H, F or Cl and where m is an integer and has values from 3 to 7, or where R" is not present if a double bond is present on the carbon atom adjacent to the OH; and
  c) obtaining 5-hydroxymethylfurfural.

Preferably, a process is provided for producing 5-hydroxymethylfurfural comprising the following steps:
  a) providing fructose,
  b) acid-catalyzed, three-fold cleavage of water from the fructose provided in step a) in a bisphasic reaction system comprising water and hexafluoroisopropanol in the ratio by volume from 1:2 to 1:4, preferably 1:3, in the presence of a mineral acid, preferably HCl, in an amount of 5 to 8 mol/L, preferably 6.4 mol/L, at a temperature of 60 to 70° C., preferably 65° C., for a period of 30 to 60 minutes, preferably 38 minutes,
  c) obtaining 5-hydroxymethylfurfural.

Preferably, a process is provided for producing furfural comprising the following steps:

a) providing at least one xylose-containing and/or arabinose-containing carbohydrate or a derivative thereof, preferably xylose and/or arabinose,
  b) acid-catalyzed cleavage of water from the at least one xylose-containing and/or arabinose-containing carbohydrate or derivative thereof provided in step a), preferably xylose and/or arabinose, preferably after cleavage of at least one glycosidic bond, in a biphasic reaction system, wherein one phase comprises predominantly water and the other phase comprises at least one multi-fluorinated alcohol compound having the structural formula I below:

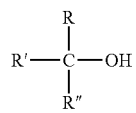

where
  (i) R, R' and R" are mutually independently selected from the group consisting of H, aryl, alkyl, alkenyl, alkynyl, F, —$CF_2X$, —$C_nF_{2n}X$, —$C_nF_{2n-2}X$, wherein at least two of the radicals R, R' and R" are other than H, aryl, alkyl, alkenyl and alkynyl, n is an integer and has values from 2 to 6 and X=H, F or Cl, or
  (ii) R and R' are covalently bonded to each other and form a chain having an empirical formula which is selected from the group consisting of —$C_mF_{2m-1}X$, —$C_mF_{2m-2}X$, —$C_mF_{2m-3}X$, —$C_mF_{2m-4}X$ and —$C_mF_{m-1}X$ and where R" is selected from the group consisting of H, aryl, alkyl, alkenyl, alkynyl, F, —$CF_2X$, —$C_nF_{2n}X$ and —$C_nF_{2n-2}X$, where n is an integer and has values from 2 to 6, where X=H, F or Cl and where m is an integer and has values from 3 to 7, or where R" is not present if a double bond is present on the carbon atom adjacent to the OH; and
  c) obtaining furfural.

Preferably, a process is provided wherein the multi-fluorinated alcohol compound is selected from the group consisting of 2,2,3,3,3-pentafluoropropan-1-ol, 2-allyl-hexafluoroisopropanol, 1H,1H-heptafluorobutan-1-ol, 2,2,3,4,4,4-hexafluorobutan-1-ol, 2,2,3,3,4,4,5,5-octafluoropentan-1-ol, 1,1,1,3,3,3-hexafluoropropan-2-ol, 1,1,1,3,3,3-hexafluoro-2-trifluoromethylpropan-2-ol, 2,3,4,5,6-pentafluorophenol and a mixture thereof. 1,1,1,3,3,3-hexafluoro-2-trifluoromethylpropan-2-ol is also referred to as nonafluoro-tert-butyl alcohol.

Preferably, the at least one multi-fluorinated alcohol compound is selected from the group of the structural formulae below:

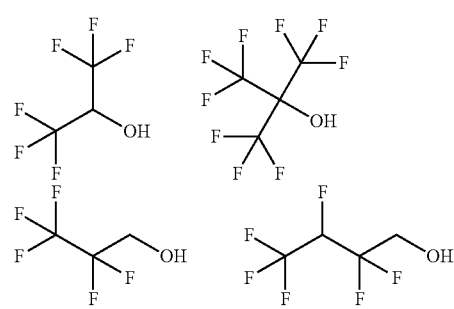

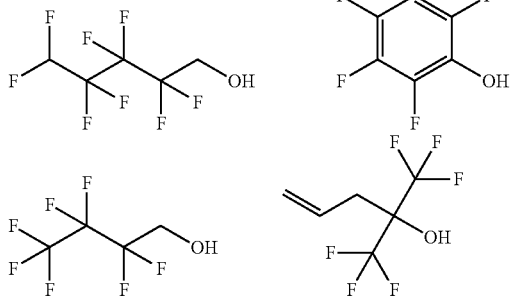

Alternatively or additionally, the multi-fluorinated alcohol compound used in the reaction system is nonafluorobutyl alcohol, pentafluorophenol, trifluoroethanol, perfluoro-1-octanol, hexafluoroisopropanol or a mixture thereof.

Preferably, a process is provided wherein the reaction system has a second phase, wherein the second phase is an aqueous phase. The reaction system, in addition to the at least one phase comprising multi-fluorinated alcohol compound, preferably has an aqueous phase. The reaction system is preferably a surfactant-free reaction system.

The phase comprising at least one multi-fluorinated alcohol compound preferably comprises at least 10% by volume, preferably at least 30% by volume, preferably at least 50% by volume, preferably at least 80% by volume of the at least one multi-fluorinated alcohol compound (at a temperature of 20° C.).

Preferably, a process is provided wherein the reaction system comprises water and the at least one multi-fluorinated alcohol compound in a ratio from 30:1 to 1:30, preferably from 10:1 to 1:10, preferably from 3:1 to 1:3, preferably 1:3 (based on the volume at a temperature of 20° C.).

Preferably, a process is provided wherein the reaction system comprises at least one acid selected from the group consisting of an organic acid, an isopoly acid, a heteropoly acid, a mineral acid, a Lewis acid and a solid having at least one acidic center, preferably Amberlyst 15.

For the acid-catalyzed water cleavage, a mineral acid and/or Lewis acid is preferably used. The mineral acid is preferably selected from hydrochloric acid, sulfuric acid, phosphoric acid and mixtures thereof. The Lewis acid is preferably selected from aluminum trichloride, zinc chloride, magnesium chloride, chromium dichloride, tin tetrachloride and boron trifluoride.

Boric acid is preferably used in addition to the mineral acid.

Preferably, a process is provided wherein the reaction system additionally has a salt. The salt is preferably selected from an alkali metal salt, aluminum trinitrate, diammonium sulfate, aluminum trichloride and a mixture thereof. The alkali metal salt is preferably lithium chloride, sodium chloride, potassium chloride, disodium sulfate, dipotassium hydrogen phosphate or a mixture thereof. Particular preference is given to disodium sulfate. By addition of salt, the phase separation, preferably of hexafluoroisopropanol, is preferably induced.

The salt is preferably added to the reaction system in an amount of 0.1 to 300 g/l, preferably 1 to 260 g/l, preferably 10 to 100 g/l.

The concentration of the at least one water cleavage compound is preferably at least 50 mmol/l, preferably at least 100 mmol/l, preferably at least 200 mmol/l, preferably at least 500 mmol/l, preferably at least 1000 mmol/l. The concentration of the at least one water cleavage compound is at most 2500 mmol/l, preferably at most 2000 mmol/l, preferably at most 1500 mmol/l.

Preferably, a process is provided wherein the water cleavage compound is present at a concentration of 10 to 4000 mmol/l, preferably 50 to 1000 mmol/l, in the reaction system, preferably in the aqueous phase.

The aqueous phase preferably comprises the acid used. In the aqueous phase, the acid, preferably mineral acid, is present preferably in an amount of 10 to 30% by weight, preferably 15 to 25% by weight. The concentration of the acid, preferably mineral acid, in the reaction system, preferably in the aqueous phase, is preferably from 2.0 to 7.0 mol/l, preferably 2.5 to 6 mol/l.

The acid-catalyzed water cleavage according to step b) is carried out preferably at a temperature of 0 to 140° C., preferably 20 to 100° C., preferably 40 to 80° C., preferably 50 to 70° C.

The duration of step b) is preferably 20 to 500 minutes, preferably 35 to 400 minutes.

5-Hydroxymethylfurfural is preferably produced from fructose. The fructose can be used preferably as monosaccharide or in the form of compounds containing fructose which release fructose under the conditions present in step b), preferably by hydrolytic cleavage. The fructose may also alternatively or additionally be obtained from compounds which contain or consist of compounds, particularly glucose, which may be isomerized to fructose.

Furfural is preferably produced from xylose and/or arabinose.

Acrylic acid is preferably produced from lactic acid.

1,3-Butadiene or methyl ethyl ketone is preferably produced from 2,3-butanediol.

Tetrahydrofuran or 1,3-butadiene is preferably produced from 1,4-butanediol.

Acrolein is preferably produced from hydroxypropionaldehyde.

2,5-Furandicarboxylic acid is preferably produced from mucic acid, also known as galactaric acid.

Preferably, a process is provided wherein the carbohydrate product obtained in step c) is 5-hydroxymethylfurfural or furfural.

The object of the present invention is also achieved by a water cleavage product produced by a process according to the invention or preferred according to the invention.

The object of the present invention is also achieved by a process for producing at least one water cleavage conversion product, wherein the process comprises the following steps:
  aa) producing at least one water cleavage product by a process according to the invention or preferred according to the invention or providing at least one water cleavage product according to the invention or preferred according to the invention,
  bb) chemical reaction of the at least one water cleavage product and
  cc) obtaining at least one water cleavage conversion product.

Preferably, a process is provided wherein the at least one water cleavage conversion product is at least one carbohydrate conversion product, at least one carbohydrate derivative conversion product or a mixture thereof.

Preferably, a process is provided wherein the at least one carbohydrate product, the at least one carbohydrate derivative product or the mixture thereof is oxidized catalytically in step bb).

Preferably, a process is provided wherein the at least one carbohydrate product, the at least one carbohydrate derivative product or the mixture thereof is hydrogenated catalytically in step bb).

Preferably, a process is provided wherein the at least one carbohydrate product is 5-hydroxymethylfurfural and is preferably oxidized catalytically and in the presence of water in step bb) to give furandicarboxylic acid or salts thereof.

Preferably, a process is provided wherein the at least one carbohydrate product is 5-hydroxymethylfurfural and is hydrogenated catalytically in step bb) to give dimethylfuran.

The object of the present invention is also achieved by a water cleavage conversion product produced by a process according to the invention or preferred according to the invention.

The object of the present invention is also achieved by the use of a multi-fluorinated alcohol compound according to the invention or preferred according to the invention, preferably having the structural formula I below,

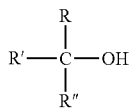

where
(i) R, R' and R" are mutually independently selected from the group consisting of H, aryl, alkyl, alkenyl, alkynyl, F, —$CF_2X$, —$C_nF_{2n}X$, —$C_nF_{2n-2}X$, wherein at least one, preferably at least two, of the radicals R, R' and R" is/are other than H, aryl, alkyl, alkenyl and alkynyl, n is an integer and has values from 2 to 6 and X=H, F or Cl, or
(ii) R and R' are covalently bonded to each other and form a chain having an empirical formula which is selected from the group consisting of —$C_mF_{2m-1}X$, —$C_mF_{2m-2}X$, —$C_mF_{2m-3}X$, —$C_mF_{2m-4}X$ and —$C_mF_{m-1}X$ and where R" is selected from the group consisting of H, aryl, alkyl, alkenyl, alkynyl, F, —$CF_2X$, —$C_nF_{2n}X$ and —$C_nF_{2n-2}X$, where n is an integer and has values from 2 to 6, where X=H, F or Cl and where m is an integer and has values from 3 to 7, or where R" is not present if a double bond is present on the carbon atom adjacent to the OH, for extracting at least one water cleavage product, produced according to the invention or in a manner preferred according to the invention, from an aqueous phase.

All statements made in connection with the process according to the invention or preferred according to the invention and all embodiments according to the invention or preferred according to the invention of the process according to the invention or preferred according to the invention also apply, mutatis mutandis, to the use of the multi-fluorinated alcohol compound for the extraction of at least one water cleavage product produced according to the invention or in a manner preferred according to the invention from an aqueous phase.

Further preferred embodiments result from the dependent claims.

The present invention is illustrated by the following examples.

1. Extraction Experiments 1.1 HMF Extraction as a Function of NaCl at Room Temperature at a Ratio by Volume (Aqueous Phase:Organic Phase) of 1:1 v/v 10 ml of an aqueous HMF solution (0.63 g/50 ml) are mixed at room temperature with 10 ml of hexafluoroisopropanol (HFIP). 0.05 g of NaCl (5 g/l) is added stepwise. Samples are withdrawn from the respective phases. The distribution coefficient is determined from the concentrations of HMF determined.

$$\text{Distribution coefficient } D_{HMF} = \frac{[c(HMF)]\text{organic phase}}{[c(HMF)]\text{aqueous phase}}$$

Table 1 shows the distribution coefficients of HMF in water:HFIP 1:1 v/v at room temperature as a function of the amount of NaCl.

| NaCl addition [g/l] | $K_{HMF}$ |
|---|---|
| 25 | 12 |
| 60 | 32 |
| 100 | 55 |
| 130 | 61 |
| 150 | 76 |
| 200 | 125 |

1.2 Extraction of Further Substances with HFIP at Room Temperature at a Ratio by Volume of 1:1 v/v (Addition of NaCl)

For each substance to be tested in Table 2, a 1.5 mol/l solution is prepared. For the substances in Table 3, substance concentrations deviating therefrom are used (see Table 3). 5 ml of the relevant solution are mixed with 5 ml of HFIP. NaCl is added stepwise until a volume distribution of about 1:2 occurs. From the concentrations determined, the respective distribution coefficient is determined.

Table 2 shows the distribution coefficients of various substances in water:HFIP 1:1 v/v at room temperature.

TABLE 2

| | NaCl addition [g/l] | Phase separation v/v | K |
|---|---|---|---|
| Acetone | 60 | 1:2.8 | 73 |
| Isopropanol | 80 | 1:2.4 | 17 |
| 1,2-Propanediol | 120 | 1:2.3 | 3 |
| Acetoin | 60 | 1:2.4 | 18 |
| Diacetyl | 80 | 1:2.3 | 17 |
| Pentanol | 100 | 1:2.7 | 53 |
| 1,5-Pentanediol | 80 | 1:2.4 | 17 |
| Methyl ethyl ketone | 120 | 1:2 | 55 |
| Glycerol | 80 | 1:2.1 | 0.45 |
| Erythritol | 40 | 1:2.2 | 0.2 |
| Glucose | 40 | 1:2.2 | 0.07 |
| Fructose | 40 | 1:2.5 | 0.15 |
| THF | 80 | 1:2.3 | 83 |
| Furan | 40 | 1:2.7 | 6 |
| Furfural | 80 | 1:2.6 | 32 |

Table 3 shows the distribution coefficients of various substances in water:HFIP 1:1 v/v at room temperature.

TABLE 3

| | Concentration [g/l] | NaCl addition [g/l] | Phase separation v/v | D |
|---|---|---|---|---|
| Ethanol | 10 | 120 | 1:2.3 | 9 |
| Butanol | 15 | 50 | 1:3.2 | 20 |

TABLE 3-continued

| | Concentration [g/l] | NaCl addition [g/l] | Phase separation v/v | D |
|---|---|---|---|---|
| Formic acid | 10 | 80 | 1:2 | 0.9 |
| Levulinic acid | 10 | 80 | 1:2 | 14 |

1.3 Use of Other Multi-Fluorinated Alcohol Compounds for the Extraction

For various substances, aqueous solutions at a concentration of 100 mmol/l are prepared in each case. 0.3 ml of the multi-fluorinated alcohol compound as extractant is added and mixed with 0.3 ml of the relevant substance solution (100 mmol/l) at room temperature.

When using HFIP, 180 g/l of NaCl are additionally added. From the concentrations determined, the respective distribution coefficient is determined.

Table 4 shows the distribution coefficients of HMF, furfural, acetone and n-butanol in various multi-fluorinated alcohol compounds, wherein the ratio of aqueous solution to the multi-fluorinated alcohol compound is 1:1 v/v at room temperature.

| | HFIP* | NFBA | PFprop | AllylHFIP | OFP | HexFB | HFB | MIBK |
|---|---|---|---|---|---|---|---|---|
| HMF | 64 | 32 | 6 | 10 | 7 | 11 | 5 | 1 |
| Furfural | 64 | 37 | 14 | 32 | >100 | 28 | 13 | 2 |
| Acetone | 61 | 45 | 19 | 24 | 24 | 0.6 | 23 | 3 |
| n-Butanol | 162 | 24 | 12 | 16 | 10 | — | — | 0.02 |

*with 180 g/l salt addition
HFIP hexafluoroisopropanol
NFBA nonafluoro-tert-butyl alcohol
Pfprop perfluoropropanol
AllylHFIP 2-allylhexafluoroisopropanol
OFP octafluoropentanol
HexFB hexafluorobutanol
HFB heptaflurobutanol
MIBK methyl isobutyl ketone 2. HMF Formation From Fructose with HCl (With and Without HFIP)

2.1 Without HFIP Extraction 4.6 ml of a fructose solution (0.39 g/10 ml) are initially charged in a 30 ml double-walled glass reactor and heated to 50° C. 5.4 ml of concentrated HCl (37%) are added with stirring. The whole reaction mixture is brought to 50° C. and the temperature and stirring are maintained over the entire course of the reaction (240 min).

Fructose conversion=49%, HMF yield=19%, HMF selectivity=39%

2.2 With HFIP Extraction 4.6 ml of a fructose solution (0.39 g/l, 217 mmol/l) and 10 ml of HFIP are initially charged in a 30 ml double-walled glass reactor and heated to 50° C. 5.4 ml of concentrated HCl (37%) are added with stirring. The whole reaction mixture is brought to 50° C. and the temperature and stirring are maintained over the entire course of the reaction (240 min).

Fructose conversion=74%, HMF yield=62%, HMF selectivity=84%

3. Various Ratios of Aqueous Phase to HFIP Phase in HMF Formation with HCl 3.1 23 ml of a fructose solution (216.6 mmol/l) and, depending on the phase ratio, 16.6 ml, 25 ml, 50 ml, 100 ml or 150 ml of HFIP are initially charged in a 300 ml glass reactor. 27 ml of HCl (37%) are added. The mixture is heated to 65° C. with vigorous stirring.

The temperature and stirring are maintained over the entire course of the reaction (38 min).

Table 5 shows the dehydration of fructose at various ratios of aqueous/HFIP phase (c(fructose)=100 mmol/l, T=65° C., HCl (21.5%, 6.5 mol/l), t=38 min).

TABLE 5

| Phase ratio used aqueous phase:HFIP phase | $C_{fructose}$ [%] | $Y_{HMF}$ [%] | S [%] |
|---|---|---|---|
| 3:1 | 63 | 46 | 73 |
| 2:1 | 75 | 63 | 84 |
| 1:1 | 86 | 72 | 83 |
| 1:2 | 94 | 80 | 85 |
| 1:3 | 99 | 96 | 97 |

C = conversion;
Y = yield;
S = selectivity

4. HMF Formation From Fructose Using Other Catalysts (With HFIP)

4.1 Sulfuric Acid ($H_2SO_4$)

61.8 ml of a fructose solution (121 mmol/l) and 75 ml of hexafluoroisopropanol are initially charged in a 300 ml glass reactor. 13.2 ml of $H_2SO_4$ (98%) are added. The mixture is heated to 70° C. with vigorous stirring. The temperature and stirring are maintained over the entire course of the reaction (400 min).

Fructose conversion=88%, HMF yield=66%, HMF selectivity=75%

4.2 Amberlyst 15 (Heterogeneous Catalyst)

1.8 g of fructose (100 mmol/l) and 18 g of NaCl (180 g/l) are dissolved in 100 ml of water. 75 ml of the fructose-NaCl solution and 75 ml of HFIP are initially charged in a 300 ml glass reactor. The heterogeneous catalyst (e.g. 1.35 g of Amberlyst 15) is added. The mixture is heated to 120° C. with vigorous stirring. The temperature and stirring are maintained over the entire course of the reaction (180 min).

Fructose Conversion=88%, HMF Yield=51%, HMF Selectivity=58%

5. Conversion of Other Substrates Using the Example of the Carbohydrate Xylose (Acid-Catalytic Water Cleavage to Give Furfural)

61.8 ml of a xylose solution (6.12 g/100 ml, 408 mmol/l) and 75 ml of HFIP are initially charged in a 300 ml glass reactor. 13.2 ml of $H_2SO_4$ (98%) are added. The mixture is heated to 120° C. with vigorous stirring. The temperature and stirring are maintained over the entire course of the reaction (120 min).

Xylose conversion=71%, furfural yield=53%, furfural selectivity=75%

6. Conversion of Other Substrates Using the Example of the Carbohydrate Glucose to Give HMF 50 ml of a glucose solution (5% by weight, 300 mmol/l), NaCl (4 g) and 50 ml of HFIP are initially charged in a 300 ml glass reactor. 0.9 g of $AlCl_3$ are added as catalyst. The mixture is heated to 130° C. with vigorous stirring. The temperature and stirring are maintained over the entire course of the reaction (120 min).

Result:

$C_{glucose}$=56%; $Y_{fructose}$=25%; $Y_{HMF}$=17%; $S_{HMF}$=30%

7. Conversion of Other Substrates Using the Example of D-arabinose to Give Furfural 41.2 ml of a D-arabinose solution (404 mmol/l) and 50 ml of HFIP are initially charged in a 300 ml glass reactor. 8.8 ml of $H_2SO_4$ (96%) are added. The mixture is heated to 120° C. with vigorous stirring. The temperature and stirring are maintained over the entire course of the reaction (90 min).

Result:

$C_{D\text{-}arabinose}$=71%; $Y_{furfural}$=47%; $S_{furfural}$=66%

8. Conversion of Other Substrates Using the Example of 1,4-Butanediol to Give Tetrahydrofuran (THF)

25 ml of HFIP, 16.4 ml of water, 2.5 mmol of 1,4-butanediol and 4.4 ml of 96% sulfuric acid are placed in a 160 ml stainless steel reactor. The mixture is heated to 120° C. with stirring at 420 rpm. The reaction time is 120 min.

Result:

$C_{1,4\text{-butanediol}}$=100%; $Y_{THF}$=89%; $S_{THF}$=89%

9. Conversion of Other Substrates Using the Example of 2,3-Butanediol to Give Methyl Ethyl Ketone (MEK)

25 ml of HFIP, 16.4 ml of water, 2.5 mmol of 2,3-butanediol and 4.4 ml of 96% sulfuric acid are placed in a 160 ml stainless steel reactor. The mixture is heated to 120° C. with stirring at 420 rpm. The reaction time is 120 min.

Result:

$C_{2,3\text{-butanediol}}$=100%; $Y_{MEK}$=25%; $S_{MEK}$=25%

10. Conversion of Other Substrates Using the Example of 3-Hydroxypropionaldehyde (3-HPA) to Give Acrolein 15 ml of HFIP, 12.6 ml of water, 1.5 mmol of 3-HPA and 2.6 ml of 96% sulfuric acid are placed in a 50 ml glass reactor. The mixture is heated to 60° C. with stirring. The reaction time is 120 min.

Result:

$C_{3\text{-HPA}}$=100%; $Y_{acrolein}$=36%; $S_{acrolein}$=36%

11. Use of Other Multi-Fluorinated Alcohol Compounds for Extracting HMF During the Reaction Using the Example of Nonafluoro-Tert-Butyl Alcohol (NFBA) Compared to HFIP In each case 9.2 ml of a fructose solution (217.7 mmol/l) are mixed with 20 ml of nonafluoro-tert-butanol (NFBA) and HFIP, respectively, in a 50 ml glass reactor. 10.8 ml of HCl (37%) are added to each of these mixtures with stirring and are heated to 30° C.

The temperature and stirring are maintained over the entire course of the reaction (24 h).

Results:
 with HFIP: fructose conversion=29%, HMF yield=21%, HMF selectivity=72%
 with NFBA: fructose conversion=28%, HMF yield=19%, HMF selectivity=68%

12. HMF Formation from Fructose in a Biphasic Mixture of OFP (Octafluoropentan-1-ol) and 1.5M HCl 20 ml of OFP and 20 ml of 1.5M HCl are placed in a 100 ml three-necked flask equipped with reflux condenser and KPG stirrer and heated to 100° C. When the reaction temperature is reached, 0.8 ml of aqueous fructose solution (450 g/l) are metered in. The mixture is stirred at 400 rpm over the entire experimental period of 120 min.

Result:

$C_{fructose}$=74%; $Y_{HMF}$=45%; $S_{HMF}$=61%

13. HMF Formation from Fructose in a Biphasic Mixture of Pfprop (2,2,3,3,3-Pentafluoropropanol) and 6.5M HCl 0.18 g of fructose and 4.2 ml of $H_2O$ are initially charged in a temperature-controlled glass reactor. 10 ml of Pfprop and 2.7 ml of HCl (37%) are added and the mixture heated to 56° C. with stirring. The reaction time is 300 min.

Result:

$C_{fructose}$=42%; $Y_{HMF}$=31%; $S_{HMF}$=74%

14. HMF Formation from Fructose in a Biphasic Mixture of Hfbutanol (2,2,3,3,4,4,4-Heptafluoro-1-Butanol) and 6.5M HCl 0.18 g of fructose and 4.2 ml of $H_2O$ are initially charged in a temperature-controlled glass reactor. 10 ml of Hfbutanol and 2.7 ml of HCl (37%) are added and the mixture heated to 56° C. with stirring. The reaction time is 300 min.

Result:

$C_{fructose}$=38%; $Y_{HMF}$=28%; $S_{HMF}$=74%

15. Induced Phase Separation by Further Electrolytes 5 ml of HFIP are added to 5 ml of an HMF solution (0.9 g/50 ml, 100 mmol/l) in a mixing cylinder. The mixture is thoroughly mixed at room temperature and phase separation is induced by adding 6 mmol of various salts (see Table 6). The distribution coefficient is determined from the HMF concentrations determined.

Table 6 shows $K_{HMF}$ and phase volume ratios of a water/HFIP system 1:1 v/v as a function of various salts (HMF solution (100 mmol/l)).

TABLE 6

| Salt | $D_{HMF}$ | Phase volume ratio |
|---|---|---|
| NaCl | 45 | 1:2.5 |
| $K_2HPO_4$ | 80 | 1:2.5 |
| $Al(NO_3)_3$ | 35 | 1:1.3 |
| $(NH_4)_2SO_4$ | 64 | 1:3.2 |
| KCl | 17 | 1:3.2 |
| $Na_2SO_4$ | 135 | 1:2.4 |
| $AlCl_3$ | 86 | 1:1.6 |
| LiCl | 37 | 1:3.2 |

16. Experiment in the Acetone-HFIP-Water System

Apart from electrolytes, phase separation in the HFIP and water system is also caused by solvents such as acetonitrile, DMSO (dimethyl sulfoxide) and acetone, and can be used as a reaction system.

20 ml of HFIP and 5 ml of acetone are placed in a 50 ml graduated flask and made up to 50 ml with water. This mixture is introduced into a 160 ml stainless steel reactor and 0.9 g of fructose and 2.6 g of Amberlyst 15 are added. The reactor is sealed and heated to 110° C. with stirring at 420 rpm. The reaction time is 120 min.

Result:

$C_{fructose}$=70%; $Y_{HMF}$=29%; $S_{HMF}$=41%

17. HMF Formation From Fructose in a Single-Phase Mixture of HFIP and Water and Also a Heterogeneous Catalyst (Amberlyst 15)

17.1 In the Batch Reactor 1.8 g of Amberlyst 15 are added to 100 ml of a solution consisting of 87.5% by volume HFIP, 12.5% by volume water and 1.8 g of fructose in a 225 ml double-walled glass reactor and the mixture is heated to 87° C. with stirring. The reaction temperature and stirring are maintained over the entire course of the experiment of 360 min.

The conversion and the yield and selectivity result from the decrease of the fructose concentration and the increase in the HMF concentration.

Result:
$C_{fructose}$=98%; $Y_{HMF}$=77%; $S_{HMF}$=79%

17.2 In the Continuous Fixed-Bed Reactor

A solution consisting of 87.5% by volume HFIP, 12.5% by volume water and 100 mmol/l fructose is pumped continuously at 0.2 ml/min via an HPLC pump through a tubular reactor via a pressure-maintaining valve into a product vessel. The 12.5 cm long and ⅜" thick tubular reactor is placed in an adjustable oven and contains a catalyst fixed bed of 5 ml of Amberlyst 15. The oven internal temperature is set to 90° C. The set flow rate gives a residence time of the reaction mixture over the catalyst of 25 min.

Due to the continuous operation, a stationary state arises after a certain time which is reflected in constant concentrations and also corresponding values for conversion, yield and selectivity.

Result:
$C_{fructose}$=99%; $Y_{HMF}$=75%; $S_{HMF}$=76%

18. Oxidation of HMF in the HFIP Phase

In a 300 ml stainless steel reactor, 83 ml of HFIP, 15 ml of water, 4 g of catalyst (0.1% Au/Pt (90:10) on $CeO_2$) and 6.4 g of NaOH are heated to 120° C. with stirring at 1200 rpm. On reaching the reaction temperature, 2 ml of an aqueous 0.5 M HMF solution is metered in and the reactor is pressurized with 20 bar oxygen. The reaction time is 240 min.

Result:
$C_{HMF}$=48%; $Y_{FDCA}$=3%, $Y_{HFCA/FFCA}$=16%, $Y_{FDA}$=16%
FDCA=2,5-furandicarboxylic acid
HFCA=5-hydroxyfurancarboxylic acid
FFCA=5-formylfurancarboxylic acid
FDA=2,5-furandialdehyde

The invention claimed is:

1. A process for producing a water cleavage product, comprising the following steps:
    a) providing at least one water cleavage compound having at least one hydroxyl group cleavable in an acid-catalyzed manner, wherein the at least one water cleavage compound is a carbohydrate or a carbohydrate derivative selected from the group consisting of sugar alcohols, sugar acids, 2-hydroxypropionic acid, 2,3-butanediol, 1,4-butanediol, hydroxypropionaldehyde, 3-hydroxypropionic acid, chitin, starch, α-amylose, glycogen, glycosaminoglycans, and mixtures thereof;
    b) acid-catalyzed cleavage of water from the at least one water cleavage compound provided in step a) in a reaction system having at least one phase and being substantially surfactant-free, wherein the at least one phase comprises at least one multi-fluorinated alcohol compound having the structural formula I below:

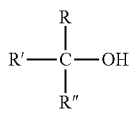

where
    (i) R, R' and R" are mutually independently selected from the group consisting of H, alkyl, alkenyl, F, —$CF_2X$, —$C_nF_{2n}X$, —$C_nF_{2n-2}X$, wherein at least one of the radicals R, R' and R" is other than H, alkyl, and alkenyl, n is an integer and has values from 2 to 6 and X=H or F provided there are at least two F atoms per molecule; and
    c) obtaining at least one water cleavage product produced according to step b).

2. The process as claimed in claim 1, wherein the at least one carbohydrate is a compound containing hexose and/or pentose.

3. The process as claimed in claim 2, wherein the hexose and/or pentose is selected from the group consisting of fructose, glucose, arabinose and xylose.

4. The process as claimed in claim 1, wherein the multi-fluorinated alcohol compound is selected from the group consisting of 2,2,3,3,3-pentafluoropropan-1-ol, 1H,1H-heptafluorobutan-1-ol, 2,2,3,3,4,4,5,5-octafluoropentan-1-ol, 1,1,1,3,3,3-hexafluoropropan-2-ol, and 1,1,1,3,3,3-hexafluoro-2-trifluoromethylpropan 2 ol.

5. The process as claimed in claim 1, wherein the reaction system has a second phase, wherein the second phase is an aqueous phase.

6. The process as claimed in claim 1, wherein the reaction system comprises water and the at least one multi-fluorinated alcohol compound in a ratio from 30:1 to 1:30.

7. The process as claimed in claim 1, wherein the reaction system comprises at least one acid selected from the group consisting of an organic acid, an isopoly acid, a heteropoly acid, a mineral acid, a Lewis acid and a solid having at least one acidic center.

8. The process as claimed in claim 1, wherein the reaction system further comprises a salt.

9. The process as claimed in claim 1, wherein the at least one water cleavage compound is present at a concentration of 10 to 4000 mmol/L in the reaction system.

10. The process as claimed in claim 1, wherein the cleavage product obtained in step c) is 5-hydroxymethylfurfural or furfural.

11. The process as claimed in claim 1, wherein at least one of the R, R', or R" is immobilized on a support material.

12. A process for producing at least one water cleavage conversion product, wherein the process comprises the following steps:
    aa) producing at least one water cleavage product by a process as claimed in claim 1,
    bb) chemically reacting the at least one water cleavage product by catalytical oxidation or catalytical hydrogenation to yield at least one conversion product, and
    cc) obtaining and separating the at least one conversion product.

13. The process as claimed in claim 12, wherein the at least one water cleavage product is 5-hydroxymethylfurfural and is oxidized catalytically in the presence of water in step bb) to give furandicarboxylic acid or salts thereof.

14. The process as claimed in claim 12, wherein the at least one water cleavage product is 5-hydroxymethylfurfural and is hydrogenated catalytically in step bb) to give dimethylfuran.

15. The process as claimed in claim 8 wherein the salt is an alkali metal salt.

16. The process as claimed in claim 1 wherein the at least one water cleavage compound is present at a concentration of 10 to 4000 mmol/L in an aqueous phase in the reaction system.

17. The process as claimed in claim 1 wherein the carbohydrate is selected from the group consisting of fructose, difructose, trifructose, inulin, sucrose, isomaltulose, oligofructose, glucose, isomaltulose, cellobiose, cellulose, starch, hydrolyzed starch, amylopectin, arabinose, and xylose, and mixtures thereof.

18. The process as claimed in claim 1 wherein the at least one water cleavage product is 5 hydroxymethylfurfural, and wherein the at least one water cleavage compound is selected from glucose, fructose, glucose containing carbohydrate, and a fructose containing carbohydrate.

19. The process as claimed in claim 1 wherein the at least one water cleavage product is 5 hydroxymethylfurfural, and wherein the at least one water cleavage compound is fructose, and wherein the reaction system is biphasic comprising water and hexafluoroisopropanol.

20. The process as claimed in claim 1 wherein the at least one water cleavage product is furfural, and wherein the at least one water cleavage compound is selected from xylose, arabinose, a xylose containing carbohydrate, and an arabinose containing carbohydrate.

21. The process as claimed in claim 1 wherein the at least one multi-fluorinated alcohol compound is selected from the group consisting of

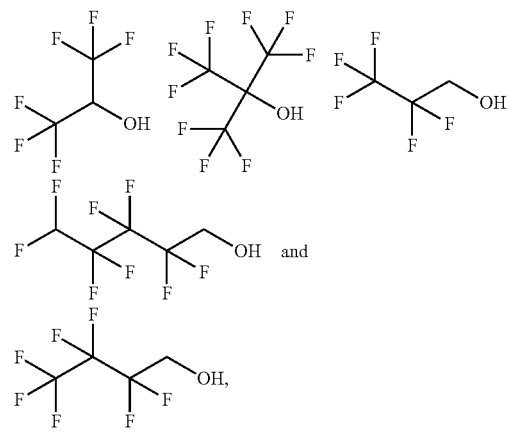

and mixtures thereof.

22. The process as claimed in claim 1 wherein the at least one multi-fluorinated alcohol compound is selected from the group consisting of nonafluorobutyl alcohol, pentafluorophenol, trifluoroethanol, perfluoro-1-octanol, hexafluoroisopropanol, and mixtures thereof.

* * * * *